(12) United States Patent
Fukuta et al.

(10) Patent No.: US 8,431,042 B2
(45) Date of Patent: Apr. 30, 2013

(54) SOLID STATE SCINTILLATOR MATERIAL, SOLID STATE SCINTILLATOR, RADIATION DETECTOR, AND RADIATION INSPECTION APPARATUS

(75) Inventors: Yukihiro Fukuta, Yokohama (JP); Takao Sawa, Yokohama (JP); Makoto Hayashi, Yokohama (JP)

(73) Assignees: Kabushiki Kaisha Toshiba, Toyko (JP); Toshiba Materials Co., Ltd., Yokohama-shi (JP)

( * ) Notice: Subject to any disclaimer, the term of this patent is extended or adjusted under 35 U.S.C. 154(b) by 0 days.

(21) Appl. No.: 13/401,210

(22) Filed: Feb. 21, 2012

(65) Prior Publication Data

US 2012/0145962 A1 Jun. 14, 2012

(51) Int. Cl.
  *C09K 11/08* (2006.01)
  *C09K 11/77* (2006.01)
(52) U.S. Cl.
  USPC .................................................. 252/301.4 R
(58) Field of Classification Search ............. 252/301.17, 252/301.4 R; 250/370.11
  See application file for complete search history.

(56) References Cited

U.S. PATENT DOCUMENTS

| | | | |
|---|---|---|---|
| 4,525,628 A | 6/1985 | DiBianca et al. | |
| 6,630,077 B2 * | 10/2003 | Shiang et al. | 252/301.4 R |
| 7,094,362 B2 * | 8/2006 | Setlur et al. | 252/301.4 F |
| 8,083,968 B2 | 12/2011 | Fukuta et al. | |
| 2003/0127630 A1 * | 7/2003 | Vartuli et al. | 252/301.4 R |
| 2010/0294939 A1 * | 11/2010 | Kuntz et al. | 250/361 R |

FOREIGN PATENT DOCUMENTS

| | | |
|---|---|---|
| EP | 0 097 300 A1 | 1/1984 |
| JP | 58-204088 A | 11/1983 |
| JP | 59-027283 A | 2/1984 |
| WO | WO 2009/113379 A1 | 9/2009 |

* cited by examiner

*Primary Examiner* — Emily Le
*Assistant Examiner* — Lynne Edmondson
(74) *Attorney, Agent, or Firm* — Foley & Lardner LLP

(57) ABSTRACT

In an embodiment, a solid state scintillator material includes a composition represented by a general formula: $(Gd_{1-\alpha-\beta-\gamma}TB_\alpha Lu_\beta Ce_\gamma)_3(Al_{1-x}Ga_x)_a O_b$, where $\alpha$ and $\beta$ are numbers satisfying $0<\alpha\leq0.5$, $0<\beta\leq0.5$, and $\alpha+\beta\leq0.85$, $\gamma$ is a number satisfying $0.0001\leq\gamma\leq0.1$, $x$ is a number satisfying $0<x<1$, $a$ is a number satisfying $4.8\leq a\leq5.2$ and $b$ is a number satisfying $11.6\leq b\leq12.4$ (atomic ratio), and a garnet structure.

14 Claims, 2 Drawing Sheets

SOLID STATE SCINTILLATOR MATERIAL, SOLID STATE SCINTILLATOR, RADIATION DETECTOR, AND RADIATION INSPECTION APPARATUS

FIELD

Embodiments described herein relate generally to a solid state scintillator material, a solid state scintillator, a radiation detector, and a radiation inspection apparatus.

BACKGROUND

In the field of medical diagnosis and industrial inspection, inspections using a radiation inspection apparatus such as an X-ray computed tomography apparatus (X-ray CT apparatus) are in practice. The X-ray CT apparatus has a structure that an X-ray tube (X-ray source) emitting a fan-shaped X-ray beam and an X-ray detector in which plural X-ray detecting elements are arranged are disposed to face each other with a sectional plane of a subject as a center between them. In the X-ray CT apparatus, the fan-shaped X-ray beam is emitted from the X-ray tube to the X-ray detector, and an angle is varied by one degree at a time with respect to the sectional plane every time the beam is emitted to obtain X-ray absorption data. The X-ray absorption data is analyzed by a computer to calculate an X-ray absorption rate of each position on the sectional plane, and an image is constructed according to the X-ray absorption rates.

The X-ray detector in the X-ray CT apparatus includes a solid state scintillator which emits visible light when excited by X-rays. The solid state scintillator is a monocrystalline scintillator or a polycrystalline ceramic scintillator. An X-ray detector composed of the solid state scintillator and a photodiode is now under development. By using the X-ray detector using the solid state scintillator, it is easy to increase the number of channels while making the detecting elements compact, and the X-ray CT apparatus can be made to have higher resolution.

Known examples of the solid state scintillator used for the X-ray detector include monocrystalline bodies such as cadmium tungstate ($CdWO_4$), sodium iodide (NaI) and cesium iodide (CsI), and polycrystalline ceramics such as europium-activated barium fluorochloride (BaFCl:Eu), terbium-activated lanthanum oxybromide (LaOBr:Tb), thallium-activated cesium iodide (CsI:Tl), calcium tungstate ($CaWO_4$), cadmium tungstate ($CdWO_4$), europium-activated gadolinium oxide ($Gd_2O_3$:Eu) and praseodymium-activated gadolinium oxysulfide ($Gd_2O_2S$:Pr).

Rare earth oxysulfide ceramics such as $(Gd_{1-x}Pr_x)_2O_2S$ ($0.0001 \leq x \leq 0.01$) and $(Gd_{1-x-y}Pr_xCe_y)_2O_2S$ ($0.0001 \leq 0.01$, $0 \leq y \leq 0.005$) have characteristics such as a large X-ray absorption coefficient and a short afterglow time of light emission. Apart from the above, rare earth oxide ceramics having a garnet structure is also known as a solid state scintillator. The rare earth oxide ceramics having a garnet structure has a characteristic that light output is excellent. However, the X-ray CT apparatus is desired that an exposure dose of a subject is further reduced. Therefore, it is demanded that the solid state scintillator material is more sensitive and its afterglow time is reduced in order to reduce the scan time.

On the other hand, as a measure for terrorism prevention in the airport attracting attention in these days, the solid state scintillator most commonly used in the security fields such as a luggage inspection system or the like is a monocrystalline body of cadmium tungstate. In comparison with the rare earth oxysulfide ceramics or the rare earth oxide ceramics having a garnet structure, the monocrystalline body of cadmium tungstate is inferior in characteristics but superior in view of cost because its cost is low. But, the monocrystalline scintillator of cadmium tungstate has a possibility of worsening the environment because cadmium (Cd) is a noxious substance.

DETAILED DESCRIPTION

Figure 1:
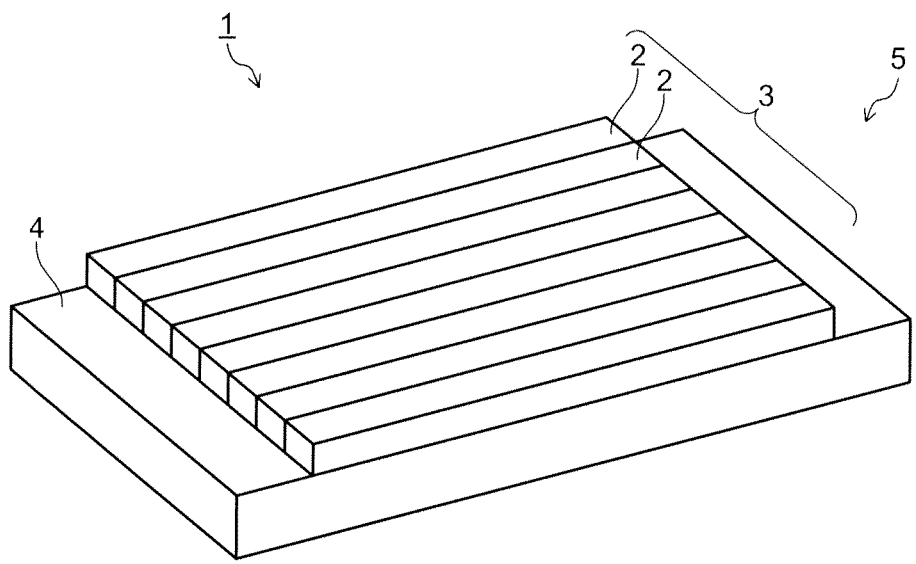
FIG. 1 is a perspective view showing a radiation detector according to a first embodiment.

According to one embodiment, there is provided a solid state scintillator material having a composition represented by a general formula:

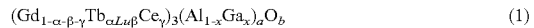

$$(Gd_{1-\alpha-\beta-\gamma}Tb_\alpha Lu_\beta Ce_\gamma)_3(Al_{1-x}Ga_x)_a O_b \quad (1)$$

where, $\alpha$ and $\beta$ are numbers satisfying $0<\alpha\leq 0.5$, $0<\beta\leq 0.5$, and $\alpha+\beta\leq 0.85$ (atomic ratio), $\gamma$ is a number satisfying $0.0001\leq\gamma\leq 0.1$ (atomic ratio), x is a number satisfying $0<x<1$ (atomic ratio), a is a number satisfying $4.8\leq a\leq 5.2$ (atomic ratio), b is a number satisfying $11.6\leq b\leq 12.4$ (atomic ratio). The solid state scintillator material of the embodiment includes a garnet structure.

A solid state scintillator material and a solid state scintillator according to a embodiment are described below. The solid state scintillator material is a phosphor material which is a raw material for the solid state scintillator described later. The solid state scintillator material includes an oxide (garnet type oxide) having a garnet structure. The garnet type oxide has a basic structure represented by $R_3A_5O_{12}$, where R is a rare earth element, A is at least one element selected from Al and Ga, and O is oxygen. The rare earth element R in the formula (1) is gadolinium (Gd), terbium (Tb), lutetium (Lu), and cerium (Ce). The solid state scintillator material may contain a rare earth element in a range of 50 mass ppm or less other than the above element.

Gd, Tb and Lu are elements which occupy 4 coordination sites. The electron beam irradiation surface of an X-ray tube target is mostly made of tungsten or tungsten alloy such as Re-W alloy. The X-ray tube has a mechanism to emit X-rays when the electron beam irradiation surface made of tungsten or tungsten alloy is irradiated with the electron beam. Gd has the highest absorption coefficient of X-rays emitted from tungsten, and it is preferable as a constituent element of the solid state scintillator material. Therefore, in the formula (1), the content of Gd with respect to the whole amount (total amount of Gd, Tb, Lu and Ce) of the rare earth elements R is determined to be an amount exceeding zero ($0<1-\alpha-\beta-\gamma$). In addition, the content of Gd with respect to the whole amount of the rare earth elements R is preferably 20 atomic % or more ($0.2 \leq 1-\alpha-\beta-\gamma$) to obtain the garnet structure stably, and to improve the absorption of X-rays by the solid state scintillator material.

Tb is an element which forms together with Gd a basic structure of the garnet-type oxide and also contributes to light emission. The Tb content ($\alpha$) with respect to the whole amount of the rare earth elements R is determined to be in a range of exceeding zero and 50 atomic % or less ($0<\alpha\leq 0.5$). In this case, an afterglow characteristic of the solid state scintillator material is improved. If the Tb content ($\alpha$) exceeds 50 atomic %, no further effect can be obtained, and since the ratio of the other rare earth elements decreases, the characteristics are degraded. To improve the light-emitting property and the afterglow characteristic, the Tb content ($\alpha$) with respect to the whole amount of the rare earth elements R is preferably in a range of 10 atomic % or more and 48 atomic % or less ($0.1 \leq \alpha \leq 0.48$), and more preferably in a range of 20 atomic % or more and 30 atomic % or less ($0.2 \leq \alpha \leq 0.3$).

Lu is an element which suppresses the precipitation of a hetero-phase in the garnet-type oxide. Examples of the hetero-phase in the garnet-type oxide include a perovskite phase (R(Al,Ga)O$_3$ phase) and a monoclinic phase (R$_4$(Al,Ga)$_2$O$_9$ phase). Specific examples of the perovskite phase include GdAlO$_3$. Specific examples of the monoclinic phase include a Gd$_4$Al$_2$O$_9$ phase. Especially, the perovskite phase tends to precipitate as a hetero-phase in the garnet-type oxide. When the precipitation amount of the perovskite phase increases, light scattering tends to occur, and the characteristics of the solid state scintillator material formed of the garnet-type oxide are degraded.

When Lu is used as one of the rare earth elements R forming the garnet-type oxide, the precipitation of the hetero-phase represented by the perovskite phase can be suppressed. Therefore, it is possible to improve the characteristics such as emission intensity and the like of the solid state scintillator material. It is determined that the Lu content ($\beta$) to the whole amount of the rare earth elements R is in a range of exceeding zero and 50 atomic % or less ($0 < \beta \leq 0.5$). When the Lu content ($\beta$) is in the above range, the characteristics such as emission intensity and the like of the solid state scintillator material are improved. When the Lu content ($\beta$) exceeds 50 atomic %, no further effect can be obtained, and since the ratio of the other rare earth elements decreases, the characteristics are degraded.

To obtain the effect of suppressing the precipitation of the hetero-phase in the garnet-type oxide with good reproducibility, the Lu content ($\beta$) with respect to the whole amount of the rare earth elements R is preferably 1 atomic % or more. The Lu content ($\beta$) is preferably 49 atomic % or less to secure the Gd content or the like. Thus, the Lu content ($\beta$) with respect to the whole amount of the rare earth elements R is preferably in a range of 1 atomic % or more and 49 atomic % or less ($0.01 \leq \beta \leq 0.49$), and more preferably in a range of 20 atomic % or more and 49 atomic % or less ($0.2 \leq \beta \leq 0.49$).

If a total amount ($\alpha+\beta$) of the Tb content ($\alpha$) and the Lu content ($\beta$) with respect to the whole amount of the rare earth elements R becomes excessively large, the Gd content decreases relatively, and it becomes difficult to obtain the basic structure of the garnet-type oxide and the absorption of X-rays by the solid state scintillator material might decrease. Therefore, the total amount ($\alpha+\beta$) of Tb and Lu with respect to the whole amount of the rare earth elements R is determined to be 85 atomic % or less ($\alpha+\beta \leq 0.85$). It is more preferable that the total amount ($\alpha+\beta$) of Tb and Lu is 70 atomic % or less ($\alpha+\beta \leq 0.7$).

Ce is an element causing the garnet-type oxide to emit light. Even if a Ce content ($\gamma$) with respect to the whole amount of the rare earth elements R is less than 0.01 atomic % or exceeds 10 atomic %, light emission of the solid state scintillator material formed of the garnet-type oxide becomes weak. Therefore, the Ce content ($\gamma$) with respect to the whole amount of the rare earth elements R is determined to be in a range of 0.01 atomic % or more and 10 atomic % or less ($0.0001 \leq \gamma \leq 0.1$). The Ce content ($\gamma$) is more preferably in a range of 0.1 atomic % or more and 1 atomic % or less ($0.001 \leq \gamma \leq 0.01$).

Aluminum (Al) and gallium (Ga) are elements essential to form the garnet structure. The Al and Ga each serve as a single element to form the garnet structure. But, when the Al is used alone, impurities (e.g., Ba) are easily contained. Meanwhile, when the Ga is used alone, light emission becomes weak, and a cost might become high. Therefore, the garnet-type oxide forming the solid state scintillator material of the embodiment contains both the Al and Ga. Accordingly, the Ga content (x) with respect to the total content of the Al and Ga in the formula (1) is determined to be in a range of exceeding zero and less than 100 atomic % ($0 < x < 1$).

In addition, to achieve both the effect of reducing the impurity content and the effect of improving the light-emitting property, the Ga content (x) with respect to the total content of Al and Ga is preferably in a range of 1 atomic % or more and 80 atomic % or less ($0.01 \leq x \leq 0.8$). If the Ga content (x) is less than 1 atomic %, the effect of decreasing the impurity content might not be obtained satisfactorily. On the other hand, if the Ga content (x) exceeds 80 atomic %, the light-emitting property tends to decrease, and the manufacturing cost tends to increase. The Gd content (x) is more preferably in a range of 10 atomic % or more and 60 atomic % or less ($0.1 \leq x \leq 0.6$).

For a composition analysis of the garnet-type oxide, it is determined to perform the quantitative analysis of Gd, Tb, Lu, Ce, Al and Ga according to alkali fusion-ICP emission spectrometry. It is determined that the quantitative analysis of oxygen is performed according to an inert gas fusion-infrared absorbing method.

In the garnet-type oxide which forms the solid state scintillator material, the garnet structure has a stoichiometric composition which is originally represented by R$_3$A$_5$O$_{12}$ (R: rare earth element, A: Al, Ga). Even if the garnet phase has a composition which somewhat deviates from the stoichiometric composition, the characteristics of the solid state scintillator material can be obtained. Therefore, when it is assumed that a total atomic number of the rare earth elements R is 3, a total atomic number a of the Al and Ga is determined to be in a range of $4.8 \leq a \leq 5.2$. Deviation of the total atomic number a of the Al and Ga from the above range results in a tendency of precipitating the hetero-phase such as the perovskite phase. The total atomic number, a of the Al and Ga is preferably in a range of $4.9 \leq a \leq 5.1$.

When it is assumed that the total atomic number of the rare earth elements R is 3, it is determined that the atomic number b of oxygen is in a range of $11.6 \leq b \leq 12.4$. Deviation of the atomic weight b of oxygen from the above range results in a tendency of precipitating the hetero-phase such as the perovskite phase. The atomic number b of oxygen is preferably in a range of $11.8 \leq a \leq 12.2$. It is determined that the total atomic number (=3) of the rare earth elements R is a total atomic weight of Gd, Tb, Lu and Ce. Even if other rare earth elements are contained, their contents are small to be 50 mass ppm or less, so that it need not be counted as the atomic weight of the rare earth element R.

It is preferable that a content of barium (Ba) contained as an impurity in the garnet-type oxide forming the solid state scintillator material is preferably 400 mass ppm or less (including zero). A content of fluorine (F) as an impurity is preferably 300 mass ppm or less (including zero). If the Ba content exceeds 400 mass ppm or the F content exceeds 300 mass ppm, transparency of the solid state scintillator is degraded, and light emission tends to vary.

The Ba reacts with the Al easily, and there is a possibility that the Ba reacts with the Al to form a hetero-phase before the garnet phase is formed. Therefore, the Ba content is preferably determined to be 400 mass ppm or less, and more preferably 200 mass ppm or less. But, the Ba easily produces a liquid phase as BaF, thereby providing an effect of activating a production reaction of the garnet phase. The garnet-type oxide may contain Ba in a range of 10 to 400 mass ppm, and further in a range of 10 to 200 mass ppm. The F content is preferably zero (detection limit or less). It is determined that the Ba content is quantified according to the alkali fusion-ICP emission spectrometry, and the F content is quantified according to a thermal hydrolysis separation-ion chromatography.

In manufacturing the solid state scintillator material formed of the garnet-type oxide, it is preferable that a flux such as barium fluoride ($BaF_2$) or aluminum fluoride ($AlF_3$) is used as a reaction accelerator. Especially, $BaF_2$ is effective for manufacturing the garnet-type oxide. But, in the garnet-type oxide using Al only, Ba and F are easily contained into particles during the process of their growth. In addition, the Ba and F tend to react with the Al, and a $BaAlO_x$ compound (x is mainly 3) or the like is readily generated as a hetero-phase. On the other hand, the solid state scintillator material of the embodiment uses both the Al and Ga. Thus, the Ba and F can be prevented from being contained more than necessary in the solid state scintillator material (garnet-type oxide).

As described above, it is preferable that the precipitation amount of the hetero-phase, such as the perovskite phase, of the garnet-type oxide forming the solid state scintillator material is small. Specifically, when the solid state scintillator material is undergone X-ray diffraction analysis, a ratio ($I_P/I_G$) of the maximum peak intensity $I_P$ of the perovskite phase with respect to the maximum peak intensity $I_G$ of the garnet phase is preferably 0.01 or less (including zero). If the ratio $I_P/I_G$ exceeds 0.01, the ratio of the hetero-phase becomes large, and scattering of light is generated, and the characteristics of the scintillator tend to become low. The ratio $I_P/I_G$ of the solid state scintillator material is more preferably zero (detection limit or less). It is determined that the X-ray diffraction analysis of the solid state scintillator material is performed using Cu as a target with a voltage of 40 kV, a current value of 40 mA, and a scan speed of 1.0°/min.

When the ratio ($I_P/I_G$) between the maximum peak intensity (height) $I_G$ of the garnet phase and the maximum peak intensity (height) $I_P$ of the perovskite phase is 0.01 or less (including zero) by the X-ray diffraction analysis, it means that the perovskite phase which is a hetero-phase is very small. For all hetero-phases (such as the monoclinic phase) other than the perovskite phase, the maximum peak intensity is also compared with the garnet phase, and it is preferable that the intensity ratio is 0.01 or less and more preferable that it is zero (detection limit or less). That is, it is preferable that the hetero-phase is not present. When the garnet-type oxide not containing or substantially not containing the hetero-phase is used, the emission intensity (light output) and the transparency of the solid state scintillator material can be improved.

In addition, it is preferable that when the solid state scintillator material is excited by X-rays, the maximum emission peak is in a range of 530 to 560 nm. It is seen that the maximum emission peak is based on a sharp emission spectrum of the Tb, and the Tb contributes to light emission. Use of both the sharp emission spectrum of the Tb and the broad emission spectrum of the Ce can provide a solid state scintillator having high light output and short afterglow (decay time of afterglow is short). The existence of the maximum emission peak in the above range indicates that the garnet-type oxide does not substantially have a hetero-phase but has a stable crystalline structure. In addition, when the solid state scintillator formed of the garnet-type oxide is used to form a radiation detector, matching with a photodiode which is a photoelectric conversion element is improved, and sensitivity of the detector can be enhanced.

The solid state scintillator of the embodiment is described below. The solid state scintillator of the embodiment is provided with a polycrystalline body of the oxide (garnet-type oxide) having the composition represented by the above-described formula (1) and the garnet structure. That is, the solid state scintillator is provided with the polycrystalline body which is formed of a sintered body of the solid state scintillator material of the above embodiment. The solid state scintillator material of the embodiment can be formed into the polycrystalline body without using a sintering aid such as silicon oxide. Therefore, there is substantially no change in the composition and the ratio of the hetero-phase between the solid state scintillator material and the solid state scintillator as its polycrystalline body.

In other words, the solid state scintillator has the composition represented by the formula (1). The Ba content of the solid state scintillator is same as that of the solid state scintillator material. The Fe content is also the same. The ratio ($I_P/I_G$) of the maximum peak intensity $I_P$ of the perovskite phase with respect to the maximum peak intensity $I_G$ of the garnet phase in the X-ray diffraction analysis and the maximum emission peak when excited by X-rays also have the same characteristics as those of the solid state scintillator material. Specific numerical values are as described above. The above-described emission intensity, transparency, afterglow characteristic and the like can be realized according to the solid state scintillator having the above composition, constituent phase, impurity concentration, characteristics and the like. Therefore, it is possible to realize the radiation detector such as an X-ray detector with high sensitivity and an increased scan speed. Since the specific characteristics are already described above, overlapped descriptions are omitted.

It is preferable that the polycrystalline body forming the solid state scintillator has an average crystal grain diameter in a range of 2 to 50 μm. When the polycrystalline body has an average crystal grain diameter of less than 2 μm, it means that there are a large number of crystal particles having a small crystal particle diameter. Therefore, the ratio of a crystal grain boundary increases, and a light transmission rate tends to decrease. It is preferable that the average crystal grain diameter of the crystalline body is large in view of increasing the light transmission rate of the solid state scintillator. But, if the average crystal grain diameter is excessively large, the polycrystalline body strength lowers. Therefore, the average crystal grain diameter of the polycrystalline body is preferably 50 μm or less. It is more preferable that the average crystal grain diameter of the polycrystalline body is in a range of 5 to 20 μm.

The average crystal grain diameter of the polycrystalline body is measured by the linear intercept method by using an SEM photograph (secondary electron image) of 2000 times magnification rate or more as a magnified photograph with a unit area of 200 μm by 200 μm. Specifically, a 200 μm straight line (line width of 0.5 mm or less) is drawn on the magnified photograph, and the number of particles on the straight line is counted. The average of crystal grain diameters is determined from a "formula: 200 μm/number of particles present on 200 μm straight line". The average value obtained by repeating the above procedure three times is determined as an "average crystal grain diameter". But, when it is difficult to determine the grain boundary, the average of crystal grain diameters may be determined from a "formula: 50 μm/number of particles present on 50 μm straight line" according to four magnified photographs with "a unit area of 50 μm by 50 μm" multiplied by four (photographs) determined as one unit area.

This procedure may be performed three times (the unit area of 50 μm by 50 μm multiplied by a total of 12 (photographs)) to determine an "average crystal grain diameter".

The relative density of the polycrystalline body is preferably 99.5% or more, and more preferably 99.9% or more and 100% or less. The relative density is determined from a "formula: (actual measured value/theoretical value) multiplied by 100(%)" according to the theoretical value which is determined from the actual measured value and a lattice constant by the Archimedean method.

It is preferable that diffuse transmittance of the solid state scintillator by light with a wavelength of 680 nm is 50% or more. Since the solid state scintillator of the embodiment does not emit light with the wavelength of 680 nm, it is a wavelength effective to measure the diffuse transmittance. If the diffuse transmittance is 50% or more, it means that transparency is high. In addition, the diffuse transmittance can be set to 60% or more by controlling the average crystal grain diameter and the relative density. It is because pores which decrease the diffuse transmittance are substantially eliminated. Since the polycrystalline body can be obtained without using the sintering aid, the crystal grain boundary is unlikely to lower the diffuse transmittance. It is determined to use a 1 mm thick solid state scintillator to measure the diffuse transmittance.

It is preferable that when the solid state scintillator is excited by X-rays, a decay time in which afterglow becomes 5% is 4 ms or less. The solid state scintillator material of the embodiment uses Tb and Ce. Therefore, there can be provided a solid state scintillator having high light output and a short afterglow time. The decay time of the afterglow indicates a time in which light output becomes 5% of the maximum value when the maximum value of the light output is set to 100% and the excitation by X-rays is terminated. When the decay time of the afterglow is set to 4 ms or less, the radiation inspection apparatus can be switched on/off in a short time. Therefore, the scan speed of the radiation inspection apparatus can be increased to make the measurement efficient.

The solid state scintillator is not limited to a particular shape. A typical shape of the solid state scintillator is a rectangular parallelepiped having a height of 0.5 mm or more and 5 mm or less, a width of 0.5 mm or more and 5 mm or less, and a length of 10 mm or more and 40 mm or less. The solid state scintillator having the above rectangular parallelepiped shape is also provided with excellent characteristics such as the above-described diffuse transmittance, short afterglow and the like.

A method of manufacturing the solid state scintillator material and the solid state scintillator of the embodiments is described below. The method of manufacturing the solid state scintillator material and the solid state scintillator is not limited to a particular one. As an efficient method of manufacturing the solid state scintillator material and the solid state scintillator, the following method can be used.

Raw materials such as gadolinium oxide ($Gd_2O_3$) powder, terbium oxide ($Tb_4O_7$) powder, lutetium oxide ($Lu_2O_3$) powder, cerium oxide ($CeO_2$) powder, aluminum oxide ($Al_2O_3$) powder, and gallium oxide ($Ga_2O_3$) powder are mixed to have a target composition so as to prepare a raw material mixture. As the raw material powder, it is preferable to use oxide powder of each element in order to obtain the garnet-type oxide efficiently.

Then, as a reaction accelerator, a flux such as barium fluoride ($BaF_2$) or the like is mixed with the raw material mixture. It is preferable that the flux is barium fluoride. When the barium fluoride is used, a garnet-type oxide having a hetero-phase in a small amount can be obtained readily. In addition, the barium fluoride is also effective for densification. The flux-mixed raw material mixture may be granulated. The added amount of the flux is preferably determined to be in a range of 2 to 6 mass parts when the raw material mixture is determined to be 100 mass parts. When the added amount of the flux is less than 2 mass parts, a sufficient reaction acceleration effect cannot be obtained. When it exceeds 6 mass parts, the flux amount is so large that the hetero-phase is formed readily.

After mixing the raw material mixture with the reaction accelerator, calcination is preferably performed at a temperature in a range of 1200 to 1800° C. When the calcination temperature is lower than 1200° C., the reaction might become insufficient. When the calcination temperature exceeds 1800° C., the temperature is so high that the barium fluoride is evaporated easily. And, the hetero-phase is formed readily. The calcination atmosphere is preferably determined to be an inert atmosphere of Ar gas or the like. If necessary, the calcination may be performed in vacuum ($10^{-2}$ Pa or less) or a reducing atmosphere. It is preferable that a calcination time is in a range of 1 to 8 hours.

When the calcination is completed, the raw material mixture becomes oxide powder having the garnet structure. The calcined garnet-type oxide powder contains the reaction accelerator remained in a large amount. For example, when barium fluoride is used as a reaction accelerator, the calcined garnet-type oxide powder contains Ba and F in a large amount. Therefore, it is preferable that the calcined oxide powder is washed to wash away the remained reaction accelerator. To perform washing efficiently, it is also effective to crush and sieve the calcined oxide powder to obtain an average grain diameter in a range of 0.5 to 20 μm.

It is preferable that the washing step is performed in combination with washing with pure water (water from which impurities were removed with an ion exchange resin) and acid washing. It is preferable to use a dilute hydrochloric acid for the acid washing. The calcined oxide powder is washed with the dilute hydrochloric acid, and then washed with pure water. The remained flux component can be removed by repeating the above procedure. The washing with pure water is preferably performed until the pure water used for washing comes to have pH 6 or more.

For example, when barium fluoride is used as a reaction accelerator, elements Ba and F remain. At this time, the calcined oxide powder is introduced in a ratio of 5 to 30 vol. % of the volume of the washing vessel, and a dilute hydrochloric acid or pure water is added to perform washing. After stirring for a predetermined time, the dilute hydrochloric acid or the pure water is discharged. This procedure is repeated several times. The F can be removed relatively easily because it reacts readily with water and becomes easily to be 300 mass ppm or less. When the washing step is repeated five or more times, the F content can be reduced to zero (detection limit or less). On the other hand, since the Ba is an element readily taken into Al, it is necessary to repeat the washing many times to reduce the Ba content to zero (detection limit or less). In addition, to reduce the Ba content to less than 10 mass ppm, it is necessary to remove the taken-in Ba. Its removal causes generation of small pores or defects, resulting in lowering the transparency. Therefore, it is preferable that the washing times are 5 to 10. The Ba content contained in the solid state scintillator material is preferably 10 mass ppm or more in view of prevention of the pores or defects from generating in the washing step.

The solid state scintillator material (phosphor powder) can be obtained by drying the washed garnet-type oxide powder. It is preferable that the average grain diameter of the garnet structure oxide powder is in a range of 0.5 to 20 μm. The solid state scintillator material is formed and sintered to produce the solid state scintillator. As the sintering method, there are a hot pressing method, an HIP method (hot isostatic pressing method), a vacuum sintering method, and the like. The sintering temperature is preferably 1400 to 1700° C., and the sintering time is preferably 1 to 10 hours. The applied pressure is preferably 20 MPa or more. The sintering atmosphere is preferably an inert atmosphere of an Ar gas or the like, or a vacuum atmosphere ($10^{-2}$ Pa or less). The sintered body obtained by the sintering becomes a polycrystalline body. The forming step is preferably performed by die pressing, rubber pressing, CIP (cold isostatic pressing) or the like.

To sinter the garnet-type oxide powder, it is preferable that a sintering aid is not used. A sintering property is improved by using a sintering aid such as $SiO_2$, but the sintering aid remains in the grain boundary and causes degradation of the transparency of the sintered body. Therefore, it is preferable that the sintering aid is not used. Since the solid state scintillator material of the embodiment is excellent in sintering property, a densified solid state scintillator (solid state scintillator having a relative density of 99.5% or more) can be obtained without using a sintering aid. In addition, when a garnet structure oxide powder having an average grain diameter in a range of 0.5 to 20 μm is used, a sintered body (polycrystalline body) having an average crystal grain diameter in a range of 2 to 50 μm can be obtained readily.

The sintered body can be used as it is as a solid state scintillator depending on a size of the obtained sintered body (polycrystalline body). When the sintered body has a large size, the sintered body is cut into a required size and used as a solid state scintillator. In other words, a large-size plate-shaped sintered body is produced, and it may be cut into a solid state scintillator. A cutout step is performed using a multiwire saw or the like. The sintered body is preferably subject to a heat treatment at a temperature of 1000 to 1400° C. for 2 to 6 hours in order for distortion removal and equalization of crystal grain diameters after the sintering step and after the cutout step. If necessary, the surface of the sintered body is polished.

The radiation detector and the radiation inspection apparatus of the embodiment are described below. FIG. 1 shows a radiation detector 1 according to a first embodiment. The radiation detector 1 has plural solid state scintillators 2, 2 . . . . The solid state scintillators 2 are made of the polycrystalline body of the garnet-type oxide according to the embodiment. The plural solid state scintillators 2 are arranged two-dimensionally via a reflection layer (not shown) to form a solid state scintillator block 3 integrated lengthwise. A photoelectric conversion element 4 is integrally disposed below the solid state scintillator block 3 to configure a solid state scintillator array 5.

Figure 2:
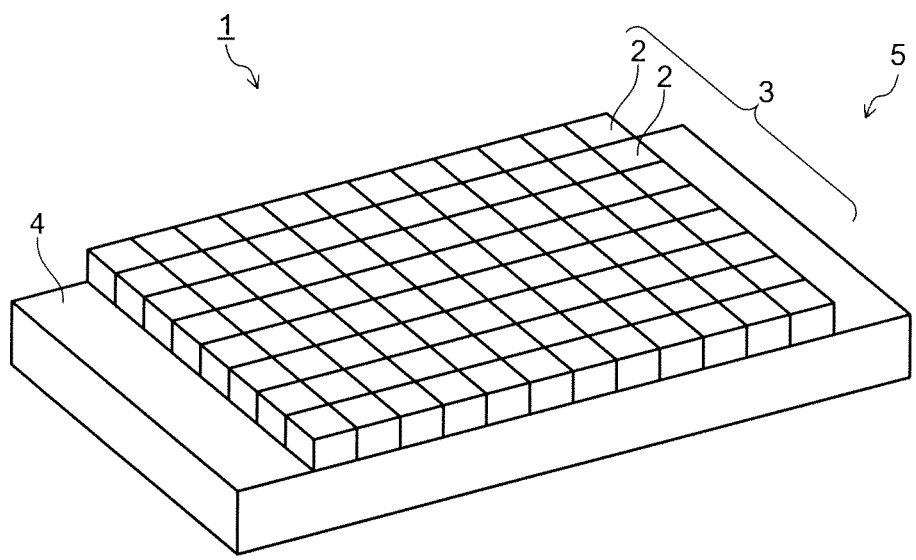
FIG. 2 is a perspective view showing a radiation detector according to a second embodiment.

The solid state scintillators 2 are not limited to the rectangular parallelepiped shape shown in FIG. 1. The solid state scintillators 2 each may have a dice shape as shown in FIG. 2. In the radiation detector 1 shown in FIG. 2, the dice shaped solid state scintillators 2 are arranged in a grid pattern via a reflection layer (not shown) to configure the solid state scintillator block 3 which is integrated lengthwise and breadthwise. As the photoelectric conversion element 4, for example a photodiode is used. The radiation detector 1 of the embodiment is configured by attaching electrical signal wires (not shown) and a collimeter (not shown) from the photoelectric conversion element 4 to the solid state scintillator array 5.

Figure 3:
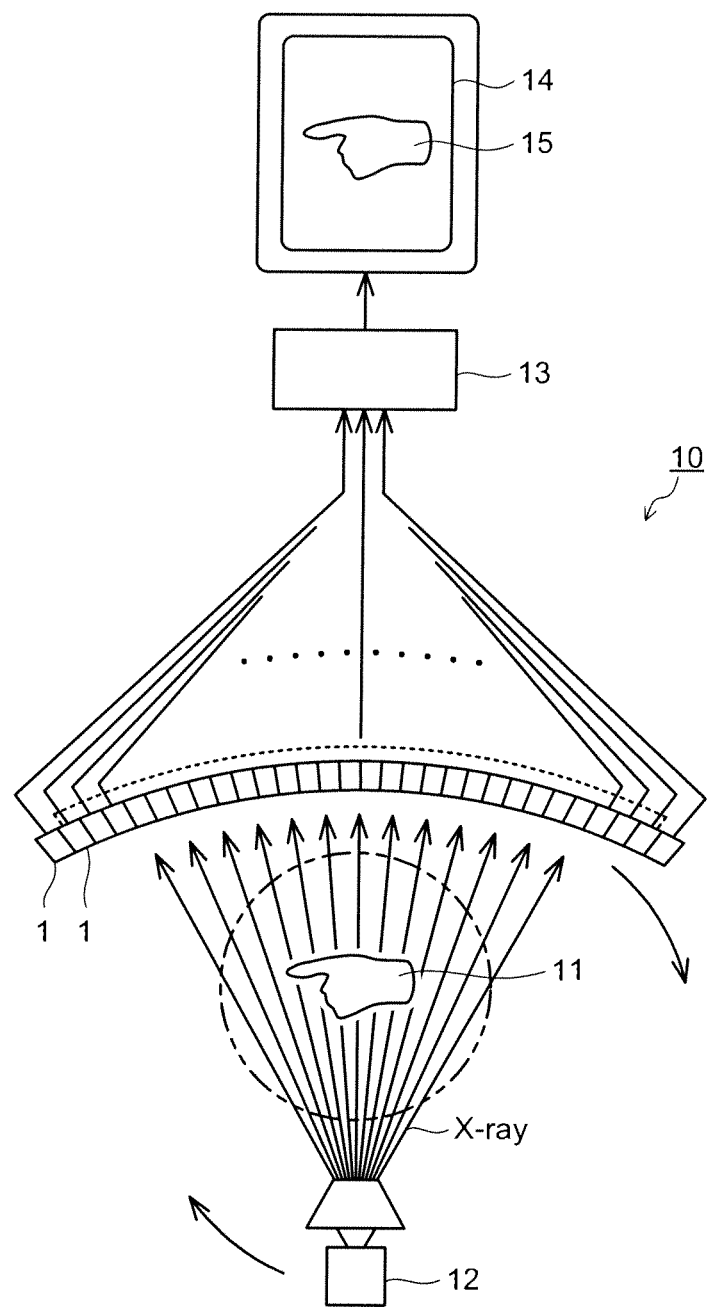
FIG. 3 is a conceptual view showing a radiation inspection apparatus according to an embodiment.

FIG. 3 shows an X-ray CT apparatus 10 which is an example of the radiation inspection apparatus of the embodiment. The X-ray CT apparatus 10 is provided with plural radiation detectors 1, 1 . . . . The radiation detectors 1 are arranged to face an X-ray tube 12 with a subject 11 between them. The X-rays emitted from the X-ray tube 12 pass through the subject 11 and reaches the radiation detectors 1. In the radiation detectors 1, the solid state scintillators 2 emit light according to the X-rays which have passed through the subject 11, and this light is converted to an electrical signal by the photoelectric conversion element 4. The electrical signal is reconstructed by a computer 13 to show a subject image 15 on a monitor 14. The X-ray CT apparatus 10 is configured so that the subject image 15 can be shown three-dimensionally by measuring around the subject 11 with an angle varied while the X-ray tube 12 is moved.

The radiation detector 1 of the embodiment is provided with the solid state scintillator 2 which is formed of a polycrystalline body of the garnet-type oxide excelling in light-emitting property and afterglow characteristic. In addition, the polycrystalline body of the garnet-type oxide forming the solid state scintillators 2 has an excellent light transmission rate and a less hetero-phase, and its grain boundary and pores are controlled. Therefore, there can be provided the radiation detector 1 having high light output and short afterglow. The X-ray CT apparatus 10 using the above radiation detector 1 makes it possible to make photographing by high-speed scanning. Therefore, X-ray photographing with high sensitivity can be realized while reducing an X-ray exposure dose of a subject. FIG. 3 shows the X-ray CT apparatus, but the radiation inspection apparatus of the embodiment is not limited to it. The radiation inspection apparatus of the embodiment can also be used effectively for an inspection apparatus not for human bodies, such as a baggage inspection system or the like.

Specific examples and evaluation results thereof are described below.

EXAMPLES 1 to 5, AND COMPARATIVE EXAMPLE 1

As raw material powders, there were prepared gadolinium oxide ($Gd_2O_3$) powder, terbium oxide ($Tb_4O_7$) powder, lutetium oxide ($Lu_2O_3$) powder, cerium oxide ($CeO_2$) powder, aluminum oxide ($Al_2O_3$) powder, and gallium oxide ($Ga_2O_3$) powder. The raw material powders were mixed in predetermined ratios, and further mixed with $BaF_2$ flux. The added amount of the $BaF_2$ flux was determined to be 4 to 5 mass parts with respect to the total amount of 100 mass parts of the raw material powder.

The mixture of the raw material powders and the $BaF_2$ flux was calcined in an Ar atmosphere under conditions of a temperature of 1400° C. and a period of 3 hours to obtain a garnet-type oxide having a composition represented by $(Gd_{0.49}Tb_{0.2}Lu_{0.3}Ce_{0.01})_3(Al_{0.6}Ga_{0.4})_5O_{12}$. It was crushed and sieved to obtain powder having an average grain diameter of 5 to 15 μm. This powder was washed by alternately using a dilute hydrochloric acid and pure water to obtain a solid state scintillator material (phosphor powder). The washing step was performed while stirring after adding the powder in 20 vol. % of the washing vessel.

It was determined that the power undergone the washing step one time was Example 1, the power undergone the washing step three times was Example 2, the power undergone the washing step five times was Example 3, the power undergone the washing step eight times was Example 4, and the power undergone the washing step ten times was Example 5. Solid state scintillator materials (phosphor powders) of the examples were obtained by performing a drying step after the washing step. In the individual examples, washing water remained after the last pure water washing had pH 6 or more.

The solid state scintillator materials of Examples 1 to 5 were measured for the Ba and F contained therein. The individual solid state scintillator materials were undergone X-ray diffraction to determine the maximum peak intensity $I_G$ of the garnet phase, the maximum peak intensity $I_P$ of the perovskite phase and their ratio ($I_P/I_G$). In addition, the individual solid state scintillator materials were excited by X-rays and measured for a maximum emission peak wavelength. The measured results are shown in Table 1. As Comparative Example 1, a garnet-type oxide solid state scintillator material (phosphor powder) having a composition represented by $(Gd_{0.5}Tb_{0.49}Ce_{0.01})_3Al_5O_{12}$ was prepared. It was also undergone the same measurements. The obtained results are also shown in Table 1.

TABLE 1

|  | Washing times [Times] | Ba content [mass ppm] | F content [mass ppm] | $I_P/I_G$ ratio | Maximum emission peak [nm] |
|---|---|---|---|---|---|
| Example 1 | 1 | 137 | 54 | 0 | 545 |
| Example 2 | 3 | 89 | 8 | 0 | 545 |
| Example 3 | 5 | 24 | 0 | 0 | 545 |
| Example 4 | 8 | 15 | 0 | 0 | 545 |
| Example 5 | 10 | 12 | 0 | 0 | 545 |
| Comparative Example 1 | 5 | 450 | 126 | 0.03 | 545 |

It is apparent from Table 1 that the solid state scintillator materials of Examples 1 to 5 had a Ba content of 10 to 400 mass ppm and an F content of 300 mass ppm or less (including zero). Since the Lu was added, a perovskite phase which was a hetero-phase was not detected. It was found as a result of the X-ray diffraction analysis that a hetero-phase other than the perovskite phase was not detected, indicating a state that the hetero-phase was not present. It was confirmed that when the washing times were five or more, the F content was zero (detection limit or less). Meanwhile, since the Lu and Ga were not used in Comparative Example 1, a hetero-phase (perovskite phase) was detected. It was also found that the Ba content and the F content were considerably large in comparison with the example in which the same washing times were performed. It is thought that the Ba was largely taken into the Al because the Ga was not used.

EXAMPLES 6 to 10, AND COMPARATIVE EXAMPLE 2

Sintered bodies (polycrystalline bodies) were produced by using the solid state scintillator materials (phosphor powders) of Examples 1 to 5 and Comparative Example 1. The sintering step was performed according to a HIP treatment under conditions of a temperature of 1600° C., a period of 3 hours, and a pressure of 50 MPa. The sintered body was cut into a size having a height of 1.5 mm, a width of 1.5 mm and a length of 25 mm with a multiwire saw. Then, a heat treatment was performed at 1200° C. for 3 hours to prepare a solid state scintillator. A sintering aid was not used in the sintering step. The solid state scintillators had the same Ba content, F content, $I_P/I_G$ ratio, and maximum emission peak wavelength when excited by X-rays as the measured values of the solid state scintillator materials.

The obtained solid state scintillators were measured for relative density, average crystal grain diameter of the polycrystalline body, and diffuse transmittance at a wavelength of 680 nm. Three magnified photographs of a unit area of 200 μm by 200 μm were used to determine the average grain diameter of the polycrystalline body according to the linear intercept method. Light of 680 nm was emitted, and diffuse transmittance was determined according to the intensity of light having passed to the back surface. The obtained results are shown in Table 2.

The solid state scintillators were used to produce radiation detectors. Ten solid state scintillators having a height of 1.5 mm, a width of 1.0 mm and a length of 25 mm were arranged via a reflection layer into an integrated body and disposed on a photodiode. Then, 120 KVp X-rays were emitted to the radiation detectors, and light output was measured. The X-rays were emitted to the scintillator surface through a 20-mm Al filter used to shield soft X-rays, and a value of current flowing through the photodiode was determined as light output. The results are shown in Table 2. The light output is shown as a relative value (%) with the light output of a $CdWO_4$ monocrystalline scintillator determined to be 100.

TABLE 2

|  | Solid state scintillator material | | Solid state scintillator | | | |
|---|---|---|---|---|---|---|
|  | Material powder | Average grain diameter [μm] | Relative density [%] | Average crystal grain diameter [nm] | Diffuse transmittance at wavelength 680 nm [%] | Light output [%] |
| Example 6 | Example 1 | 5 | 99.9 | 8 | 58 | 150 |
| Example 7 | Example 2 | 10 | 99.9 | 15 | 62 | 154 |
| Example 8 | Example 3 | 15 | 99.9 | 27 | 68 | 156 |
| Example 9 | Example 4 | 10 | 99.9 | 16 | 68 | 160 |
| Example 10 | Example 5 | 10 | 99.9 | 16 | 68 | 165 |
| Comp. Exam. 1 | Comp. Exam. 1 | 10 | 98.5 | 20 | 47 | 142 |

It is apparent from Table 2 that there were obtained solid state scintillators having a relative density of 99.5% or more without using a sintering aid according to the examples. The solid state scintillators of the examples are excellent in transmittance and light output. Meanwhile, the solid state scintillator of the comparative example had many hetero-phases and inferior transmittance. And, its light output was also inferior in comparison with the examples.

EXAMPLES 11 to 15

Gadolinium oxide ($Gd_2O_3$) powder, terbium oxide ($Tb_4O_7$) powder, lutetium oxide ($Lu_2O_3$) powder, cerium oxide ($CeO_2$) powder, aluminum oxide ($Al_2O_3$) powder, and gallium oxide ($Ga_2O_3$) powder were mixed in predetermined ratios so to have the compositions shown in Table 3, and further mixed with a $BaF_2$ flux. It was determined that the added amount of the $BaF_2$ flux was 2 to 6 mass parts with respect to a total amount of 100 mass parts of the raw material powder.

A mixture of the raw material powder and the $BaF_2$ flux was calcined in an Ar atmosphere under conditions of a temperature of 1400 to 1700° C. and a period of 2 to 5 hours to obtain garnet-type oxide powders having the compositions shown in Table 3. Then, the garnet-type oxide powders were adjusted to fall in a range of 5 to 30 vol. % of the washing vessel and undergone a repeated washing step to wash alternately with a dilute hydrochloric acid and pure water for 3 to 5 times. The production conditions are shown in Table 4. The powder undergone the washing step was crushed and sieved to control the average grain diameter. Washing water remained after the last washing with pure water had pH 6 or more. The characteristics of the obtained solid state scintillator materials were measured in the same manner as in Example 1. The results are shown in Table 5.

TABLE 3

| | Compositions |
|---|---|
| Example 11 | $(Gd_{0.199}Tb_{0.4}Lu_{0.4}Ce_{0.001})_3(Al_{0.8}Ga_{0.2})_{5.1}O_{11.9}$ |
| Example 12 | $(Gd_{0.37}Tb_{0.3}Lu_{0.3}Ce_{0.03})_3(Al_{0.6}Ga_{0.4})_{4.9}O_{12.1}$ |
| Example 13 | $(Gd_{0.49}Tb_{0.3}Lu_{0.2}Ce_{0.01})_3(Al_{0.4}Ga_{0.6})_5O_{12}$ |
| Example 14 | $(Gd_{0.48}Tb_{0.25}Lu_{0.25}Ce_{0.02})_3(Al_{0.5}Ga_{0.5})_5O_{12}$ |
| Example 15 | $(Gd_{0.39}Tb_{0.25}Lu_{0.35}Ce_{0.01})_3(Al_{0.9}Ga_{0.1})_5O_{12}$ |

TABLE 4

| | Production conditions | | |
|---|---|---|---|
| | Added $BaF_2$ amount [mass %] | Calcination temperature/time [° C./hr] | Washing times [Number of times] |
| Example 11 | 5 | 1700/4 | 5 |
| Example 12 | 5 | 1400/5 | 5 |
| Example 13 | 3 | 1600/2 | 3 |
| Example 14 | 4 | 1700/4 | 4 |
| Example 15 | 5 | 1700/4 | 5 |

TABLE 5

| | Average grain diameter [μm] | Ba content [mass ppm] | F content [mass ppm] | $I_P/I_G$ ratio | Maximum emission peak [nm] |
|---|---|---|---|---|---|
| Example 11 | 14 | 320 | 182 | 0 | 545 |
| Example 12 | 11 | 53 | 3 | 0.01 | 545 |
| Example 13 | 8 | 36 | 0 | 0 | 546 |
| Example 14 | 8 | 27 | 0 | 0 | 546 |
| Example 15 | 13 | 79 | 0 | 0.02 | 545 |

It is apparent from Table 5 that the solid state scintillator materials of Examples 11 to 15 had a hetero-phase (perovskite phase) in a small amount. Since the above-described Comparative Example 1 had the Lu content of less than 0.01, the hetero-phase (perovskite phase) was detected in a large amount. Therefore, it is seen that the Lu content is preferably 0.01 or more. In Examples 11 and 15 where the Al content is relatively large, the remained Ba content was relatively large because the Ba was taken in readily. Example 15 where the Al content was largest had a tendency that the light output decreases. Therefore, the Al content (1−x) with respect to a total content of Al and Ga is desirably in a range of more than 30 atomic and less than 90 atomic (0.3<1−x<0.9).

EXAMPLES 16 to 20

The solid state scintillator materials (phosphor powders) of Examples 11 to 15 were used to produce sintered bodies (polycrystalline bodies). The sintering step was performed under conditions of a temperature of 1400 to 1700° C., a period of 2 to 5 hours, and a pressure of 30 to 60 MPa according to the HIP treatment. The sintering conditions are shown in Table 6. A sintering aid was not used in the sintering step. The sintered bodies were cut into a size having a height of 2 mm, a width of 2 mm and a length of 25 mm with a multiwire saw to obtain solid state scintillators.

TABLE 6

| | | Sintering conditions | |
|---|---|---|---|
| | Material powder | Calcination Temperature/ time [° C./h] | Pressure [MPa] |
| Example 16 | Example 16 | 1500/5 | 50 |
| Example 17 | Example 17 | 1400/5 | 60 |
| Example 18 | Example 18 | 1500/4 | 50 |
| Example 19 | Example 19 | 1700/2 | 30 |
| Example 20 | Example 20 | 1600/3 | 30 |

The obtained solid state scintillators were measured for relative density, average crystal grain diameter of the polycrystalline body, and diffuse transmittance at a wavelength of 680 nm in the same manner as in Example 6. The results are shown in Table 7. Then, the solid state scintillators were used to produce radiation detectors. Fifteen solid state scintillators having a height of 2 mm, a width of 2 mm and a length of 25 mm were arranged via a reflection layer into an integrated body and disposed on a photodiode. The radiation detectors were measured for light output in the same manner as in Example 6. The results are shown in Table 7.

TABLE 7

| | Solid state scintillator | | | |
|---|---|---|---|---|
| | Relative Dentisy [%] | Average Crystal Grain Diameter [μm] | Diffuse Transmittance at Wavelength 680 nm [%] | Light output [%] |
| Example 16 | 99.9 | 35 | 53 | 152 |
| Example 17 | 99.9 | 3 | 51 | 146 |
| Example 18 | 100 | 14 | 67 | 158 |
| Example 19 | 100 | 22 | 69 | 162 |
| Example 20 | 99.9 | 21 | 47 | 140 |

It is apparent from Table 7 that the solid state scintillators of Examples 16 to 20 had excellent characteristics. The obtained solid state scintillators had the same Ba content, F content, $I_P/I_G$ ratio, and maximum emission peak intensity when excited by X-rays as the measured values of the solid state scintillator materials. It is because the sintering can be performed without using the sintering aid.

EXAMPLES 21 to 30, AND COMPARATIVE EXAMPLE 3

The radiation detectors of Examples 6 to 10, Examples 16 to 20 and Comparative Example 2 were used to examine the decay time during which afterglow became 5%. X-rays were emitted to the radiation detectors (solid state scintillators) by using an X-ray tube (electron beam irradiation surface is formed of Re-W alloy) which becomes an X-ray source of the X-ray CT apparatus, and the light output was increased to the maximum value of 100%. After the excitation by X-rays was terminated, a time during which the light output became 5% of the maximum value was measured. The results are shown in Table 8.

TABLE 8

| Radiation detector | | Decay time in which afterglow becomes 5% [ms] |
|---|---|---|
| Example 21 | Example 6 | 2 |
| Example 22 | Example 7 | 1 |
| Example 23 | Example 8 | 1 |
| Example 24 | Example 9 | 1 |
| Example 25 | Example 10 | 1 |
| Example 26 | Example 16 | 3 |
| Example 27 | Example 17 | 4 |
| Example 28 | Example 18 | 1 |
| Example 29 | Example 19 | 1 |
| Example 30 | Example 20 | 5 |
| Comparative Example 3 | Comparative Example 2 | 8 |

It is apparent from the above examples that the radiation detectors have a very short afterglow decay time of 4 ms or less. The radiation inspection apparatus (X-ray CT apparatus) using the above radiation detectors can be switched on/off in a short time. Therefore, high-speed scanning by the X-ray CT apparatus is made possible, and an exposure dose of a subject during examination can be reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A solid state scintillator material, comprising:
a composition represented by a general formula:

$(Gd_{1-\alpha-\beta-\gamma}Tb_\alpha Lu_\beta Ce_\gamma)_3(Al_{1-x}Ga_x)_a O_b$ where, $\alpha$ and $\beta$ are numbers satisfying $0<\alpha\leq0.5$, $0<\beta\leq0.5$, and $\alpha+\beta\leq0.85$ (atomic ratio),
$\gamma$ is a number satisfying $0.0001\leq\gamma\leq0.1$ (atomic ratio),
x is a number satisfying $0<x<1$ (atomic ratio),
a is a number satisfying $4.8\leq a\leq5.2$ (atomic ratio),
b is a number satisfying $11.6\leq b\leq12.4$ (atomic ratio); and
a garnet structure,
wherein the material contains Ba in a range of 10 to 200 mass ppm, and
wherein a ratio ($I_p/I_G$) of a maximum peak intensity $I_p$ of a perovskite phase with respect to a maximum peak intensity $I_G$ of a garnet phase by X-ray diffraction is 0.01 or less (including zero).

2. The material according to claim 1, wherein the $\alpha$ is $0.1\leq\alpha\leq0.48$, the $\beta$ is $0.001\leq\beta\leq0.49$, and the x is $0.01\leq x\leq0.8$.

3. The material according to claim 1, wherein an F content of the material is 300 mass ppm or less (including zero).

4. The material according to claim 1, wherein an emission spectrum obtained by exciting the material with X-rays has a maximum emission peak in a range of 530 to 560 nm, and includes a sharp spectrum and a broad spectrum.

5. A solid state scintillator comprising a polycrystalline body of an oxide,
wherein the oxide polycrystalline body comprises:
a composition represented by a general formula:

$(Gd_{1-\alpha-\beta-\gamma}Tb_\alpha Lu_\beta Ce_\gamma)_3(Al_{1-x}Ga_x)_a O_b$ where, $\alpha$ and $\beta$ are numbers satisfying $0<\alpha\leq0.5$, $0<\beta\leq0.5$, and $\alpha+\beta\leq0.85$ (atomic ratio),
$\gamma$ is a number satisfying $0.0001\leq\gamma\leq0.1$ (atomic ratio),
x is a number satisfying $0<x<1$ (atomic ratio),
a is a number satisfying $4.8\leq a\leq5.2$ (atomic ratio),
b is a number satisfying $11.6\leq b\leq2.4$ (atomic ratio); and
a garnet structure,
wherein the oxide polycrystalline body contains Ba in a range of 10 to 200 mass ppm, and
wherein a ratio ($I_p/I_G$) of a maximum peak intensity $I_p$ of a perovskite phase with respect to a maximum peak intensity $I_G$ of a garnet phase by X-ray diffraction of the oxide polycrystalline body is 0.01 or less (including zero).

6. The scintillator according to claim 5, wherein the $\alpha$ is $0.1\leq\alpha\leq0.48$, the $\beta$ is $0.001\leq\beta\leq0.49$, and the x is $0.01\leq x\leq0.8$.

7. The scintillator according to claim 5, wherein an F content of the oxide polycrystalline body is 300 mass ppm or less (including zero).

8. The scintillator according to claim 5, wherein an emission spectrum obtained by exciting the oxide polycrystalline body with X-rays has a maximum emission peak in a range of 530 to 560 nm, and includes a sharp spectrum and a broad spectrum.

9. The scintillator according to claim 5, wherein the oxide polycrystalline body has an average crystal grain diameter in a range of 2 to 50 μm.

10. The scintillator according to claim 5, wherein diffuse transmittance at a wavelength of 680 nm is 50% or more.

11. The scintillator according to claim 5, wherein a decay time in which afterglow becomes 5% is 4 ms or less.

12. The scintillator according to claim 5, wherein the oxide polycrystalline body has a relative density of 99.5% or more.

13. A radiation detector comprising the solid state scintillator according to claim 5.

14. A radiation inspection apparatus comprising the radiation detector according to claim 13.

* * * * *